(12) United States Patent
Chien et al.

(10) Patent No.: US 6,451,594 B1
(45) Date of Patent: Sep. 17, 2002

(54) RECOMBINANT ADENOVIRUS FOR TISSUE SPECIFIC EXPRESSION IN HEART

(75) Inventors: Kenneth R. Chien, La Jolla, CA (US); Yibin Wang, Brookville, MD (US); Sylvia Evans, Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/394,110

(22) Filed: Sep. 10, 1999

Related U.S. Application Data
(60) Provisional application No. 60/099,960, filed on Sep. 11, 1998.

(51) Int. Cl.[7] .......................... C12N 15/00; C12N 15/09; C12N 15/63; C12N 15/70; C12N 15/74

(52) U.S. Cl. .................... 435/320.1; 435/455; 536/24.1; 514/44

(58) Field of Search .............................. 435/69.1, 328, 435/320.1, 455; 536/23.5, 24.1; 514/44; 424/93.6

(56) References Cited

U.S. PATENT DOCUMENTS

| | | |
|---|---|---|
| 5,652,224 A | 7/1997 | Wilson et al. |
| 5,747,245 A | 5/1998 | Reed et al. |
| 5,772,993 A | 6/1998 | Chung et al. |
| 5,792,453 A | 8/1998 | Hammond et al. |
| 5,834,306 A | * 11/1998 | Webster et al. .......... 435/320.1 |

FOREIGN PATENT DOCUMENTS

| | | |
|---|---|---|
| WO | WO94/11506 A1 | 5/1994 |
| WO | WO96/13598 A2 | 5/1996 |
| WO | WO98/10088 A1 | 3/1998 |

OTHER PUBLICATIONS

Blau et al., "Molecular Medicine Gene therapy –A Novel Form of Drug Delivery." The New England Journal of Medicine, vol. 333 (18): 1204–1207, Nov. 1995.*
Miller et al., "Targeted vectors for gene therapy." FASEB Journal, vol. 9: 190–199, Feb. 1995.*
Anderson, F., "Human gene therapy." Nature, vol. 392 (supp): 25–30, Apr. 1998.*
Verma et al., "Gene Therapy–promises, problems and prospects." Nature, vol. 389: 239–242, Sep. 1997.*
Wold, William S. M. (1993). "Adenovirus Genes That Modulate the Sensitivity of Virus–Infected Cells to Lysis by TNF," Journal of Cellular Biochemistry 53:329–335.
Korner, Heinrich, and Burgert, Hans–Gerhard (Mar., 1994). "Down–Regulating of HLA Antigens by the Adenovirus Type 2 E3/19K Protein in a T–Lymphoma Cell Line," Journal of Virology vol. 68, No. 3, p. 1442–1448.

Gall, Jason, Kass–Eisler, Alyson, Leinwand, Leslie, and Falck–Pedersen, Erik (Apr., 1996). "Adenovirus Type 5 and 7 Capsid Chimera: Fiber Replacement Alters Receptor Tropism without Affecting Primary Immune Neutralization Epitopes," Journal of Virology vol. 70, No. 4, p. 2116–2123.
Stevenson, Susan C., Rollence, Michele, Marshall–Neff, Jennifer, and McClelland, Alan (Jun., 1997). "Selective Targeting of Human Cells by a Chimeric Adenovirus Vector Containing a Modified Fiber Protein," Journal of Virology vol. 71, No. 6, p. 4782–4790.
Kim, Steven, Lin, Hua, Barr, Eliav, Chu, Lien, Leiden, Jeffrey M., and Parmacek, Michael S. (Sep., 1997). "Transcriptional Targeting of Replication–defective Adenovirus Transgene Expression to Smooth Muscle Cells In Vivo," The American Society for Clinical Investigation, Inc. vol. 100, No. 5, p. 1006–1014.
Philip, R. et al., "Efficient and Sustained Gene Expression in Primary T Lymphocytes and Primary and Cultured Tumor Cells Mediated by Adeno–Associated Virus Plasmid DNA Complexed to Cationic Liposomes," Molecular and Cellular Biology, Apr. 1994, pp. 2411–2418, vol. 14, No. 4.
Jeyaseelan, R. et al., "A Novel Cardiac–Restricted Target for Doxorubicin," The Journal of Biological Chemistry, Sep. 5, 1997, pp. 22800–22808, vol. 272, No. 36.
Yeh, P. et al., "Advances in Adenoviral Vectors: From Genetic Engineering to Their Biology," FASEB Journal, 1997, pp. 615–623, vol. 11, No. 8.
Agah, et al., "Gene Recombination in Postmitotic Cells–Targeted Expression of Cre Recombinase Provokes Cardiac–restricted, Site–specific Rearrangement in Adult Ventricular Muscle In Vivo," J. Clin. Invest, (1997), pp. 169–179, 100.
Akhter, et al., "Restoration of β–adrenergic signaling in failing cardiac ventricular myocytes via adenoviral–mediated gene transfer," Proc. Natl. Acad. Sci. USA, (1997), pp. 12100–12105, 94.
Baldwin, et al., "Adenovirus–mediated gene transfer during initial organogenesis in the mammalian embryo is promoter– dependent and tissue–specific," Gene Ther., (1997), pp. 1142–1149, 4.
Brody, et al., "Adenovirus–Mediated in Vivo Gene Transfer," Ann. N.Y. Acad. Sci., (1994), pp. 90–101, 716.
Christensen, et al., "Physiological assessment of complex cardiac phenotypes in genetically engineered mice," Am. J. Physiol., (1997), pp. H2513–2524.

(List continued on next page.)

Primary Examiner—Scott D. Priebe
Assistant Examiner—Peter Paras, Jr.
(74) Attorney, Agent, or Firm—Brown Martin Haller & McClain (57) ABSTRACT

The present invention relates to a human type-5 recombinant adenovirus vector for achieving cardiac restricted transcription involving utilization of the cardiomyocyte-restricted cardiac ankyrin repeat protein (CARP) promoter with inclusion of the inverted terminal repeat sequences from human adeno-associated virus (AAV). Using green fluorescent protein (GFP) as a marker gene, the recombinant adenovirus vector (Ad/CG/ITR) is shown to direct transgene expression to myocardial tissue in vivo and in vitro in mouse models.

4 Claims, 2 Drawing Sheets

OTHER PUBLICATIONS

Fisher, et al., "Forced expression of the homeodomain protein Gax inhibits cardiomyocyte proliferation and perturbs heart morphogenesis," *Development*, (1997), pp. 4405–4413, 124.

Franz, et al., "Analysis of tissue–specific gene delivery by recombinant adenoviruses containing cardiac–specific promoters," *Cardiovasc. Res.*, (1997), pp. 560–566, 35.

Hajjar, et al., "Modulation of ventricular function through gene transfer in vivo," *Proc. Natl. Acad. Sci. USA*, (1998), pp. 5251–5256, 95.

Hirota, et al., "Loss of a gp130 Cardiac Muscle Cell Survival Pathway is a Critical Event in the Onset of Heart Failure during Biomechanical Stress," *J. Biol. Chem.* (1990), pp. 13809–13817, 265.

Kass–Eisler, et al., "The impact of developmental stage, route of administration and the immune system on adenovirus–mediated gene transfer," *Gene Ther.*, (1994), pp. 395–402, 1.

Kim, et al., "Transcriptional Targeting of Replication–defective Adenovirus Transgene Expression to Smooth Muscle Cell In Vivo," *J. Clin. Invest.* (1997), pp. 1006–1014, 100.

Kypson, et al., "Ex Vivo Adenovirus–Mediated Gene Transfer to the Adult Rat Heart," *J. Thorac. Cardiovasc. Surg.*, (1998), pp. 623–630, 115.

Ross, et al., "An HF–1a/ HF–1b/ MEF–2 combinatorial element confers cardiac ventricular specificity and establishes an anterior–posterior gradient of expression," *Development*, (1996), pp. 1799–1809, 122.

Rothman, et al., "Heart muscle–specific gene expression using replication defective recombinant adenovirus," *Gene Ther.* (1996), pp. 919–926, 3.

Wang, et al., "Cardiac Muscle Cell Hypertrophy and Apoptosis Induced by Distinct Members of the p38 Protein Kinase Family," *J. Biol. Chem.* (1998), pp. 2161–2618, 273.

Zou, et al. "CARP, a cardiac ankyrin repeat protein, is downstream in the Nkx2–5 homeobox gene pathway," *Development* (1997), pp. 793–804, 124.

\* cited by examiner

SEQUENCE LISTING

<160> NUMBER OF SEQ ID NOS:   3

<210> SEQ ID NO 1
<211> LENGTH: 174
<212> TYPE: DNA
<213> ORGANISM: adeno-associated virus 2

<400> SEQUENCE: 1

```
ggccactccc tctctgcgcg ctcgctcgct cactgaggcc gcccgggcaa agcccggcg      60 tcgggcgacc tttggtcgcc cggcctcagt gagcgagcga gcgcgcagag agggagtggc     120
caactccatc actagggtt cctggagggg tggagtcgtg acgtgaatta cgta            174
```

<210> SEQ ID NO 2
<211> LENGTH: 183
<212> TYPE: DNA
<213> ORGANISM: adeno-associated virus 2

<400> SEQUENCE: 2

```
catggctacg tagataagta gcatggcggg ttaatcatta actacaagga acccctagtg     60
atggagttgg ccactccctc tctgcgcgct cgctcgctca ctgaggccgg gcgaccaaag     120
gtcgcccgac gcccgggctt tgcccgggcg gcctcagtga gcgagcgagc gcgcagagag     180
gga                                                                  183
```

<210> SEQ ID NO 3
<211> LENGTH: 1026
<212> TYPE: DNA
<213> ORGANISM: Mus musculus

<400> SEQUENCE: 3

```
tcacggctgc aacatgatg gtactgagag tagaggagct ggtaacaggc aaaagaaca       60 gcaatggggc cgcaggggaa ttccttcctg gggagttcag aaatggagaa tatgaagctg     120
ctgttgcttt ggagaagcaa gaggacctga agacacttcc ggccaacagc gtgaagcagg    180
gggaggaaca acggaaaagc gagaaactgc gagaggcaga gctcaaaaag aaaaaactag    240
aacaaagatc aaagcttgaa aacttagaag accttgaaat aattgttcaa ctgaagaaaa    300
```

-continued

```
ggaaaaaata caagaaaacc aaagttccag ttgtgaagga gccagaacct gaaattatga    360
ctgaacctgt ggatgtgccg aggtttctga aagctgcgct ggagaacaaa ctgccagttg    420
tagagaaatt ggtgtcagac aagaacagcc ccgacgtctg cgatgagtat aaacggacgg    480
cactccaccg agcatgctta gaaggacact tggcgatcgt ggagaagtta atggaggctg    540
gagcccagat tgaattccga gatatgcttg aatccacagc catccactgg gcatgtcgtg    600
gaggaaacgc agatgtcctg aaactgttgc tgaacaaagg agccaaaatc agtgccagag    660
acaagcttct cagcacagcg ctgcatgtgg cggtgaggac tggtcattac gagtgcgctg    720
agcacctcat cgcctgcgag gctgatctca atgccaagga cagagaagga gacacccac    780 tgcatgatgc tgtgaggctg aaccgctata agatgattcg actcttgatg accttcggtg    840
cggacctcaa ggtcaagaac tgtgctggga agacccccat ggatctggtg ttgcactggc    900
agagtggaac caaagcaata ttcgacagcc ccaaggagaa tgcctacaag aactctcgca    960
tagctacatt ctgagaaaag agactcaaca ggagctgttc gcaggcattt tttaaagcat   1020
ttccca                                                              1026
```

RECOMBINANT ADENOVIRUS FOR TISSUE SPECIFIC EXPRESSION IN HEART

This application claims the benefit of priority of U.S. Provisional Application Serial No. 60/099,960, filed Sep. 11, 1998, which is incorporated herein by reference in its entirety.

BACKGROUND OF THE INVENTION

1. Field of the Invention

This invention relates generally to a recombinant adenoviral vector construct and to methods for the study of gene function and gene therapy for heart disease and more specifically to methods of targeting tissue specific expression of a given transgene in cardiac tissue through use of inverted terminal repeat sequences from human adeno-associated virus.

2. Background Information

Cardiovascular gene therapy represents a novel approach to the treatment of inherited and acquired heart disease. Gene transfer to the heart would allow for the replacement of defective or missing cellular proteins that are responsible for proper cardiac function. The control of in vivo cardiac function represents a complicated interplay between multiple genes, varied cell types, and environmental stimuli but the elucidation of this interplay remains dependent on a more complete understanding of the changes that occur at the molecular and cellular levels. Traditionally, the majority of human gene therapy protocols have relied on the ex vivo application of the therapeutic gene, through the introduction of a retroviral vector, to the affected cells or tissue. Because the ex vivo method of gene therapy depends on the removal from and reintroduction to the body of the target cells, the treatment of inaccessible or sensitive organs or tissue poses a major dilemma. The alternate strategy of direct in vivo delivery of therapeutic genes to the target cells represents a preferable method of gene therapy.

Targeted gene expression in somatic tissues is essential for both gene therapy and in vivo analysis of gene function, mainly through the substitution of an affected gene, using a safe and effective delivery system for the therapeutic gene. To date, recombinant adenoviruses have replaced the retrovirus as an efficient gene delivery vector for a variety of cell types and tissues (Yeh, et al., FASEB J 11, 615–23, 1997). Adenovirus vectors are highly efficient in the genetic modification of nondividing human cells and have the capacity to carry long segments of genetic information. The hurdle in using adenovirus as gene "delivery systems" is that when an adenovirus is administered to a patient to aid in the delivery of genes to specific cells, the patient's immune system may react against the virus. To overcome this hurdle, modifications have been made to make the adenoviral vector safer, less toxic to the cells and less likely to stimulate an immune response. This has involved removing the E1 region of the adenovirus gene which prevents the ability of the virus to express its own proteins required for making viral particles. In place of the E1 region, a therapeutic transgene can be inserted. The efficiency of this kind of exogenous gene delivery and subsequent expression can be high, as it does not normally integrate into the host genome, and it has a minimal effect on intrinsic host cell function (Baldwin, et al., Gene Ther. 4, 1142–49, 1997). However, while adenoviral vectors are capable of producing high levels of transgene expression, their capacity to infect and program transgene expression in large numbers of cells and tissue, including the liver and lungs, poses limitations. As a result of this high level of transient infectivity, methods have been undertaken to direct transgene expression to specific tissues or areas of the body. For cardiac tissue, a number of attempts have been reported utilizing recombinant adenoviruses to achieve transgene expression in the heart through either intra-myocardial or intra-coronary injection (Brody, et al., Ann. N.Y. Acad. Sci. 716, 90–101, 1994; Barr, et al., Gene Ther. 1, 51–8, 1994; Kypson, et al., J. Thorac. Cardiovasc. Surg. 115, 623–30, 1998). While direct injection of viral particles into the myocardium or cardiac cavity have been shown to be more efficient for gene delivery to the myocardium, infection and transgene expression also occurs in non-cardiomyocytes, which causes speculation that any specificity of transgene expression that exists is achieved by targeted delivery rather than restricted transcription (Kass, et al., Gene Ther. 1, 395–402, 1994; Kass, et al., Methods Cell Bio. 52, 423–37, 1997). As a result, ectopic expression, particularly in liver and other tissue, remains a significant limitation for the generalized use of recombinant adenoviruses for gene transfer to specific cell types within the cardiovascular and other organ systems.

In most recombinant adenoviral vectors, the E1a region of the adenovirus genome, which encodes the protein with properties for transcriptional regulation, is deleted and replaced by a minigene "cassette" that typically includes a promoter of choice, the transgene coding region, and a polyadenylation signal (Yeh, et al., FASEB J 11, 615–23, 1997). One possible approach to achieve tissue-specific transgene expression using adenoviruses is to employ cellular gene promoters that possess cell-type specificity at the transcriptional level, rather than commonly used viral gene promoters that have a high level of expression, but lack tissue specificity. In the past, a number of studies have utilized different cell promoters to achieve targeted transgene expression in various tissues, including smooth muscle (Kim, et al., J. Clin. Invest. 100, 1006–14, 1997), pancreas (Dusetti, et al., J. Biol. Chem. 272, 5800–4, 1997), endothelium (Morishita, et al., J. Biol. Chem. 270, 27948–53, 1995), lung (Strayer, et al., Am. J. Respir. Cell Mol. Bio. 18, 1–11, 1998), and several kinds of tumors ( Su, et al., Proc. Natl. Acad. Sci. USA 94, 13891–6, 1997; Siders, et al., Cancer Res. 56, 5638–46, 1996). Similar attempts using cardiac-specific promoters such as the myosin light chain-2 (MLC-2v) and the alpha-myosin heavy chain (α-MHA) promoters, in the context of adenoviruses, however, have not been wholly successful in providing tissue-restricted gene expression in vivo (Kim, et al., J. Clin. Invest. 100, 1006–14, 1997). These results suggest that adenoviral genomic sequences surrounding the deleted E1a region may be responsible for at least partial specificity of the adjacent cellular promoter. It has also been suggested that sequences around the E1a region may contain negative regulatory elements that act in modulating the specificity and activity of a cellular promoter (Shi, et al., Hum. Ther. 8, 403–10, 1997). This undesirable property of adenoviral vectors has limited their application, especially in the context of in vivo studies where tissue specific expression of the transgene is required.

Thus, the need remains for a transgene expression system utilizing recombinant adenoviral vectors that are tissue specific for use in in vivo and in vitro gene therapy and gene function analysis for both neonatal and adult subjects. The present invention satisfies this need and provides related advantages as well.

SUMMARY OF THE INVENTION

The present invention provides a human type-5 recombinant adenovirus vector to achieve cardiac restricted transcription in both neonatal and adult subjects utilizing the cardiomyocyte-restricted cardiac ankyrin repeat protein (CARP) promoter in cooperation with the inverted terminal repeat (ITR) sequences from human adeno-associated virus (AAV). Such a combination is effective in achieving cardiac tissue-specific transcription of the transgene both in vitro and in vivo.

The invention further provides a method to achieve tissue targeted expression of a given transgene in cardiac tissues in both neonatal and adult subjects. Such a method has significant applications in both gene function studies and gene therapy for inherited and acquired heart diseases.

DETAILED DESCRIPTION OF THE PREFERRED EMBODIMENT

The present invention provides a means for achieving cardiac restricted transcription of a transgene in both neonatal and mature cardiac tissues through the use of a recombinant adenoviral gene delivery vector which is engineered to contain a cardiomyocyte-restricted CARP promoter in conjunction with inverted terminal repeat sequences from human adeno-associated virus, the sequences of which are incorporated herein by reference. In the construction of adenovirus vectors, it is most common to delete the majority of the E1a and E1b regions of the serotype 5 adenovirus gene to prevent replication of the adenoviral DNA. A prototypical vector is constructed by inserting the desired exogenous genetic information, including the left hand end inverted terminal repeat (ITR), signal enhancers, promoters for the expression of the desired exogenous gene, and a polyadenylation signal, into the former E1 position of the adenovirus. Fu, et al. (*Nat. Biotechnol.* 1 6, 253–7, 1998) incorporated herein by reference, have reported an unusual property of the inverted terminal repeat (ITR) sequences, specifically of adenoassociated virus (AAV). Adeno-associated viruses are satellite viruses derived from replication-deficient parvovirus and most often found in association with adenovirus or herpes simplex virus. The wild-type AAV is non pathogenic and can site specifically integrate into a host genome, can transduce nondividing cells, and does not induce an immune response which could destroy the transduced cells. Fu, et al. have shown that the inclusion of both the left and right end segments of the AAV-ITR sequences imparts the ability to enhance the level as well as tissue specificity of the transgene expression using viral gene promoters or tissue-specific cellular gene promoters in developing Xenopus embryos. Further, Philip, et al. (*Mol. Cell Bio.* 14, 2411–8, 1994) have demonstrated that the inclusion of both the left and right end AAV-ITR sequences in mammalian plasmid constructs results in the enhancement of efficiency and stability of transgene expression. In the context of a recombinant adenovirus vector, inclusion of both the left and right end ITR sequences from adeno-associated virus has the ability to enhance tissue specificity of the exogenous transgene expression when a cardiac restricted promoter is utilized.

In order to achieve targeted gene expression in the cardiac tissue, the 213 base pair, 5' flanking promoter fragment of the CARP gene was selected to direct the transgene expression. Three separate lines of transgenic mice were created which harbored various CARP promoter/β-galactosidase reporter genes for the purpose of studying this 5' flanking CARP promoter. CARP, a cardiac ankyrin repeat protein, is a putative downstream regulatory gene in the homeobox gene Nkx2-5 pathway which regulates the expression of the ventricular myosin light chain-2 (MLC-2v) gene (Zou, et al., *Development* 124, 793–804, 1997). Studies have identified an essential GATA-4 binding site in the proximal upstream regulatory region of the CARP gene and cooperative transcriptional regulation mediated by Nkx2.5 and GATA-4. This cooperative regulation is dependent on the binding of GATA-4 to its cognate DNA sequence in the promoter, which suggests that Nkx2.5 may exert its control on the CARP promoter, at least in part through GATA-4. As used herein, the term "homeobox gene Nkx2-5" refers to the murine homologue of Drosophila gene tinman which has been previously shown to be required for heart tube looping morphogenesis and ventricular chamber-specific myosin light chain-2 expression during mammalian heart development. Ventricular myosin light chain-2 (MLC-2v), one of the earliest markers of ventricular regionalization during mammalian cardiogenesis, has been the subject of numerous studies seeking to identify the molecular pathways that guide cardiac ventricular specification, maturation and morphogenesis. These studies have identified a 28 base pair HF-1a/MEF-2 cis-element in the MLC-2v promoter region which appears to confer the cardiac ventricular chamber-specific gene expression during cardiogenesis as well as showing that the ubiquitous transcription factor YB-1 binds to the HF-1a site in conjunction with a co-factor. Moreover, data further indicates that regulatory elements within the 5' flanking region of the CARP gene are capable of directing region-specific (atrial vs. ventricular and left vs. right) transgene expression in the heart. The 213 base pair sequence element in the 5' flanking region of the CARP gene appears to be sufficient to confer conotruncal-specific transgene expression.

CARP forms a physical complex with YB-1 in cardiac myocytes and endogenous CARP seems to be localized in the cardiac myocyte nucleus. Zou, et al. (*Development* 124, 793–804, 1997) have demonstrated that CARP can negatively regulate HF-1-TK minimal promoter activity in an HF-1 sequence-dependant manner in cardiac myocytes as well as displaying transcriptional inhibitory activity when fused to a GAL4 DNA-binding domain in both cardiac and non-cardiac cells. Analysis using a standard Northern-blot protocol indicates an enriched level of CARP mRNA in the myocytes of cardiac tissue, and to a lesser degree in skeletal muscle, and that endogenous CARP expression can be upregulated in heart and other tissue upon induction of cytokine activity (Chu, et al., *J. Biol. Chem.* 270, 10236–45, 1995; Jeyaseelan, et al., *J. Biol Chem.* 272, 22800–8, 1997).

Cytokines play a critical role in the control and maintenance of the signaling pathways that regulate mammalian physiology in multiple organ systems. Their widespread importance is reflected in the extensive tissue distribution of cytokine networks, where a deficiency in cytokine signaling components can result in multiple organ defects. In a study by Hirota, et al. (*Cell* 97, 1 89–198, Apr. 16, 1999) incorporated herein by reference, researchers explored the role of IL-6 related cytokines in the pathogenesis of cardiac failure, which is the leading cause of combined morbidity and mortality in the United States and other developed countries. In response to chronic increases in blood pressure and blood volume overload, as is common in myocardial injury, the heart responds by becoming enlarged in order to maintain normal cardiac function, a process known as compensatory hypertrophy. CT-1, a member of the IL-6 cytokine family, can activate the onset of myocyte hypertrophy in vitro and has been shown to be vital as a potent myocyte survival factor in cardiac muscle cells by blocking the onset of cardiomyocyte apoptosis. There is further evidence that the presence of cytokine receptor gp130 expression in cardiac myocytes can lead to compensatory cardiac hypertrophy, thus delaying the onset of cell apoptosis and ultimately, heart failure. A deficiency in the gp130 cytokine receptor signaling pathway often results in severe cardiac defects in developing embryos possibly leading to an early lethality in utero. A therapeutic strategy of introducing the transgene coding region of gp130 directly into the embryonic heart cells using the tissue specific adenoviral vector delivery system of the present invention, while still in utero, may be a viable treatment option. Similarly, introduction of the gp130 gene into mature cardiac myocytes under constant biomechanical stress, through attachment to the cardiac specific CARP promoter of the present invention, may initiate expression of the gp130 cytokine receptor pathway, resulting in enhanced cardiac compensatory hypertrophy, offsetting cardiomyocyte apoptosis, and thus averting cardiac failure.

Generation of Recombinant Adenovirus Vectors

The recombinant adenovirus vector of the present invention was constructed through homologous recombination between shuttle plasmid DNA containing the transgene and pJM17 plasmid DNA containing the entire genome of the human type-5 adenovirus, the method of construction described by Wang, et al., *J. Biol. Chem.* 273, 2161–8, 1998, for the generation of Adenovirus/CMV vectors. The *E. coli* host containing plasmid pJM17 that includes DNA of the entire genome replication defective human type-5 adenovirus has been deposited as ATCC Accession No. PTA-1047 in the American Type Culture Collection, 10801 University Blvd., Manassas, Va. 20110–2209, U.S.A., under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted.

The shuttle plasmid, pAdv/CARP, was assembled with a 2.5 kilobase CARP promoter, excised from the 5° flanking region of the CARP gene and inserted between the Bam H I and Xho I sites of pXCJL.2. (The *E. coli* host containing plasmid pJM 17 including DNA of the entire genome of the human type-5 adenovirus containing the insert murine CARP promoter sequence has been deposited as ATCC Accession No. PTA-1046.) The resulting construct was shown to be sufficient to confer cardiac-restricted marker gene expression in cultured cells and transgenic mice. (See Zou, et al. (*Development* 124, 793–804, 1997).)

With the elucidation of CARP function, this 2.5 kilobase CARP promoter was thus used to generate an adenovirus/CARP/marker construct, using a green fluorescent protein (GFP) gene as a visual reporter for identification of adenovirus/CARP promoter activity following in vitro and in vivo administration of the adenovirus construct. To construct the reporter gene, GFP coding sequences were excised from pEGFP-N1 (Clontech, Calif.) through Bam HI and Afl III digestion, and inserted into the Xho I site of pAdv/CARP to generate pAdv/CG. The resulting recombinant adenovirus was designated Adv/CG.

Figure 1:
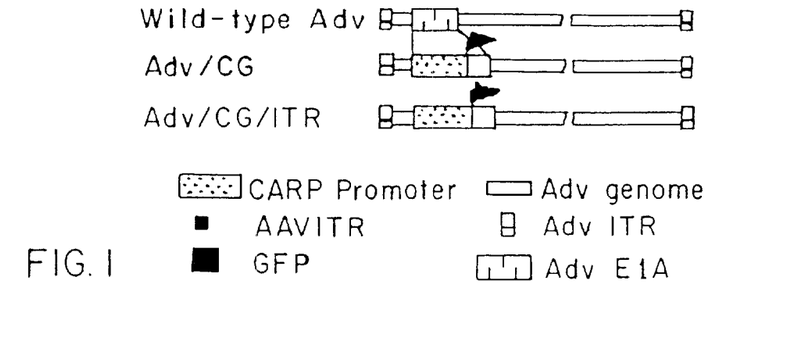
FIG. 1 shows the constructs of recombinant adenovirus vectors. All recombinant adenovirus vectors were generated through homologous recombination between pJM17 plasmid DNA and the specific shuttle plasmid DNA in 293 cells.

In order to determine whether inclusion of AAV ITR sequences in the adenovirus genome has the ability to enhance tissue specific expression of the transgene, the DNA fragment containing the CARP promoter and GFP coding sequences was removed from pAdv/CG through Bam HI and Sal I digestion and subsequently inserted into the Xho I site of the pAdv/AAV plasmid, which is derived from pXCJL.2 containing two copies of the AAV ITR sequence. The resulting plasmid, pAdv/CG/ITR, was used to generate a recombinant adenovirus, designated as Adv/CG/ITR, using transformation techniques known to those in the art. FIG. 1 provides a diagrammatic representation of the recombinant adenovirus constructs. All recombinant adenovirus vectors were plaque-purified using standard methods and analyzed by PCR for the presence of the transgene in the viral genome. High titer viral stocks were prepared by a single ultracentrifugation on a CsCI gradient as described by Wang, t al., *J. Biol. Chem.* 273, 2161–8, 1998, the technique well known in the art.

Cardiomyocytes and Cardiac Fibroblast Culture and Adenovirus Infection

To establish the cardiac tissue specificity of the adenoviral vector of the present invention, primary ventricular myocytes and cardiac fibroblasts were prepared from 1–2 day old Sprague-Dawley rats using a Percoll gradient method as described by Iwaki, et al., *J. Biol. Chem.* 265, 13809–17, 1990. Cardiac fibroblasts were isolated from the upper band of the Percoll gradient, and subsequently plated in high glucose Dulbecco's modified Eagle's medium supplemented with 10% fetal bovine serum. Myocytes were isolated from the lower band of the Percoll gradient and subsequently plated in 4:1 Dulbecco's modified Eagle's medium; 199 medium, 10% horse serum and 5% fetal bovine serum. The cardiac fibroblasts and myocytes were infected with the recombinant adenovirus at varied multiplicity of infection (M.O.I.) 24 hours after isolation and were then incubated for an additional 48 hours before being subject to DNA, RNA, and fluorescent photomicroscopic analysis.

RNA and DNA Analysis

RNA samples were prepared from cultured cells and mouse tissues using RNAzol B solution according to the manufacturer's protocol (TEL-TEST, Texas). Northern blot hybridization was performed according to a standard protocol, familiar to those of skill in the art, using GFP coding sequences to generate a $p^{32}$ labeled probe. Total DNA, purified from cultured cells and mouse tissues, were prepared using the protocol as directed by a Purogene DNA isolation kit, and then digested with the restriction enzymes Xho I/Not I for Southern blot analysis using the same $P^{32}$ labeled GFP coding sequence probes as used in the Northern blot hybridization.

In vivo Adenoviral Injection into Neonatal Mouse Heart

Using the procedure of high efficiency, long term expression via adenoviral vector injection into neonatal mouse as described by Brody, et al., *Ann. N.Y. Acad. Sci.* 716, 90–101, 1994, 1-day old mouse neonates were anesthetized by hypothermia at 4° C. for 2 minutes. 10 µl of viral solution, containing $2 \times 10^9$ viral particles, were injected directly into the cardiac cavity using a flame stretched capillary tube mounted on a micromanipulator. Flashback of pulsatile blood in the capillary tube gave positive indication of correct intracavitary placement. The subject neonatal mice were allowed to recover by rewarming at room temperature and were then placed back with the mother for a 48 hour period. At the end of the 48 hours, the neonatal mice were sacrificed, and the heart and liver were removed from the body for DNA, RNA and fluorescent photomicrographic analysis.

Mouse Embryo Culture and Microinjection of Adenovirus Vector

The preparation of rat serum was by the method as described by Cockroft, et al., *Dissection and Culture of Post-Implantation Embryos,* 1990 (IRL Press, Oxford, England). Whole mouse embryos were cultured according to the method of Sturm and Tam, Methods Enzymol. 225, 164–90, 1993. As per the protocol, timed pregnant female mice were sacrificed by cervical dislocation. The uterus was dissected from the body and rinsed in phosphate buffered-saline (PBS) to remove any residual blood and then transferred to a sterile receptacle containing PB1 media (137 mM NaCl; 2.7 mM KCl; 0.5 mM $MgCl_2$; 8.04 mM $Na_2HPO_4$, 1.47 mM $KH_2PO_4$; 0.9 mM $CaCl_2$; 0.33 Na pyruvate; 1 g/L glucose; 0.01 g phenol red, pH 7.35; 100 ml/L streptomycin; 100 U/ml penicillin; all reagents from Sigma Biochemicals, St. Louis, Mo.). Embryos of 11 days post coitum (E11) were dissected from the uterus and the decidual and Riechert's membrane removed. The embryos were separated from the yolk sac and amnion, which had been left attached during dissection to ensure continuity of the vessels connecting the embryo to the yolk sac or the umbilical vessels from the embryo to the placenta. The isolated embryos were then transferred to pre-equilibrated media (consisting of 50% rat serum which was continuously gassed (95% $O_2$, 5% $CO_2$)) in roller culture bottles placed on a rocker table and incubated at 37° C. After one hour in culture, the embryos were placed in a petri dish and microinjected into the left ventricle using a 6 µm diameter glass pipette. The micropipettes had been previously prepared using a multistage pipette puller (Suter Instrument Co., Novato, Calif.) to pull 1 mm glass capillary tubes into the 6 µm needle configuration. Each micropipette was attached to a MX-110-R 4 axis, manual micromanipulator (Newport Instruments, Newport, Calif.) using electrode holders. Intracardiac injection of 1 µl of a high titer viral solution ($2 \times 10^8$) proceeded at a low-flow rate, on the order of 0.2 to 0.5 µl per second (2 to 5 seconds for one microliter.)

The ability to target transgene expression in in vivo cardiomyocytes represents a new and powerful approach to study and manipulate specific gene function during the process of cardiac development as well as the treatment of heart disease using gene therapeutic technology. The strategy of using a cardiac-restricted cellular promoter in combination with both the right and left hand ITR sequences from AAV (SEQ ID NO:1 and SEQ ID NO:2, respectively) to achieve cardiac specific transgene expression in both embryonic and post-natal heart tissue distinguishes the present invention from other recombinant adenoviral vectors currently found in the art. Further, the inclusion of both AAV-ITR sequences in the context of a cardiac-restricted recombinant adenovirus vector preserves the tissue-specificity of the cellular promoter activity both in vitro and in vivo and, when combined with a targeted delivery system, makes the present invention significant as gene based therapy to treat heart disease as well as providing a method to study specific gene function in embryonic and post-natal heart.

As previously reported in the studies of Fu, et al. and Phillip, et al., the presence of AAV-ITR sequences in mammalian cell systems, as well as in developing Xenopus embryos, has the effect of enhancing transgene expression. The reports of studies of Fu, et al. and Phillip, et al. are incorporated herein by reference. While experiments in Xenopus embryos suggest that ITR sequences facilitate DNA segregation among replicating cells, other studies implicate AAV-ITR sequences in enhancing genomic integration after transfection, at least in an in vitro setting.

Regardless of the mode of action, adenovirus DNA remains mostly in episomal form in infected cells. Since cardiac myocytes, on their own, do not demonstrate robust replication after birth, it is unlikely that these two properties contribute significantly to the enhancement of tissue specificity in heart tissue. An alternative mechanism that has also been implicated in Xenopus studies is that AAV-ITR has insulating properties that shield the flanked transgene from the effects of other regulatory elements within the adenoviral genome. In fact, this mode of action has support from findings establishing the existence of negative regulatory elements located around the adenovirus E1a region that can modulate the specificity of the adjacent cellular promoter. Two previous studies from Franz, et al. (Cardiovasc. Res. 35, 560–6, 197) and Rothman, et al. (Gene Ther. 3, 919–26, 1996) have also reported the generation of cardiomyocyte-specific adenoviruses using the MLC-2v promoter but not with α-MHC promoter even though both promoters have cardiomyocyte-specific transcriptional activity. The reports of studies of Franz, et al. and Rothman, et al. are incorporated herein by reference. The lack of transgene expression of Adv/CG (CARP promoter without AAV ITR) indicates that the specific transcriptional activity of a cellular promoter is subject to significant influence by the surrounding adenovirus genome. Therefore, inclusion of AAV ITR provides a general strategy to achieve tissue-specific transcription using other cellular promoters.

Hammond, et al. (U.S. Pat. No. 5,792,453) have reported a replication defective adenovirus vector comprising a transgene coding for an angiogenic protein or peptide that can be targeted to the myocardium of a patient by intracoronary injection directly into the coronary arteries, for the treatment of myocardial ischemia. In order to deliver these angiogenic proteins, which may include aFGF, bFGF, FGF-5 (fibroblast growth factors) and VEGF (vascular endothelial growth factor), Hammond, et al. rely on ventricular myocyte-specific promoters, namely the promoters from MLC-2v and α-MHC, to achieve targeted delivery. However, as has been established by the method of the present invention, myocardial expression of the angiogenic transgene in the cardiomyocytes is more likely the result of direct cardiac application of the adenoviral vector rather than the use of the MLC-2v or α-MHC promoters. In addition to the CARP gene promoter (SEQ ID NO: 3), the AAV-ITR sequences (SEQ ID NOS: 1 and 2) of the present invention can be used with other cardiac restricted promoters, including:

1. α-myosin heavy chain gene
2. β-myosin heavy chain gene
3. Myosin light chain 2v gene
4. Myosin light chain 2a gene 5. CARP gene
6. Cardiac α-actin gene
7. Cardiac m2 muscarinic acetylcholine gene
8. ANF
9. Cardiac troponin C
10. Cardiac troponin I
11. Cardiac troponin T
12. Cardiac sarcoplasmic reticulum Ca-ATPase gene
13. Skeletal α-actin
14. Artificial cardiac promoter derived from MLC-2v gene The AAV-ITR sequences can also be used to generate other target vectors for conditional gene expression by using inducible promoters. The inclusion of the AAV-ITR sequences of the present invention, in the adenoviral vector of Hammond, et al. would assure the tissue specific expression of the angiogenic transgene and, thus, avoid the negative effects these angiogenic proteins have on other tissues in the body.

The following examples are intended to illustrate but not limit the present invention.

EXAMPLE 1

Cell-type Specific Transcription Mediated by Adv/CG/ITR Vector in Cultured Cells This example provides an evaluation of transcriptional specificity of the recombinant adenovirus containing the cardiomyocyte enriched CARP promoter coupled (SEQ ID NO: 3) with the inverted terminal repeat sequences (ITR) from human adeno-associated virus (AAV) (SEQ ID NOS: 1 and 2).

Purified adenoviral vectors were used to infect cultured primary cardiac fibroblasts and ventricular myocytes prepared from neonatal rat heart. An adenovirus vector with a human cytomegalovirus (CMV) enhancer/promoter driving GFP expression (Adv/CMV/GFP) was used as a positive control for viral infection and GFP detection. As previously reported by Wang, et al., *J. Biol. Chem.* 273, 2161–8, 1998, recombinant adenoviruses are capable of efficiently infecting many cell types, including cardiomyocytes, at a low multiplicity of infection (M.O.I.) of less than 100 viral particles/cell and the expression of GFP can be readily detected at a high level in more than 95% of cardiomyocytes cultured from neonatal rat hearts. Cardiac fibroblasts, however, require an M.O.I. of more than 1,000 viral particles/cell in order to achieve approximately 70% of infection. Using the same level of viral infection (100 or 1,000 viral particles/cell), GFP expression was not detected in either myocytes or fibroblasts infected with the Adv/CG vector. In contrast, when the Adv/CG/ITR vector was used as the infecting agent, GFP expression was observed in more than 90% of the cardiac myocytes, but not at any appreciable levels in cardiac fibroblasts. These results demonstrate that the cardiac specific CARP promoter/AAV-ITR is necessary to achieve transcriptional specificity of the transgene in the ventricular myocytes of cultured neonatal rat heart while transcriptional expression is not found in the fibroblasts even at even high M.O.I.

Figure 2:
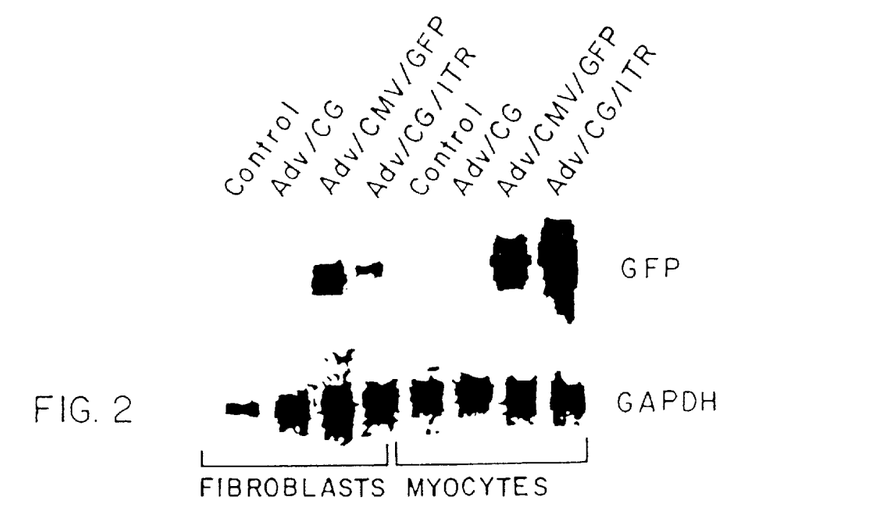
FIG. 2 shows a Northern-blot analysis of the relative cell-type specific transcription of GFP in cultured cells following adenovirus infection. RNA from uninfected, control and infected cardiac myocytes were subject to Northenblot analysis using GFP coding sequences as a probe and normalized by hybridization signals for GAPDH mRNA.

Further evaluation of cardiac-restricted expression of GFP by Adv/CG/ITR at the transcriptional level was performed using a standard Northern-blot protocol for mRNA detection. As seen in FIG. 2, the levels of GFP mRNA in Adv/CMV/GFP infected cardiomyocytes and cardiac fibroblasts are readily detectable. In Adv/CG infected cells, however, the GFP mRNA was not detected, which was in agreement with the observations from evaluation by fluorescent photomicroscopy. In contrast, RNA samples from cardiomyocytes infected with Adv/CG/ITR showed significant levels of GFP transcript, while RNA samples from infected cardiac fibroblasts has significantly lower levels of GFP.

Figure 3:
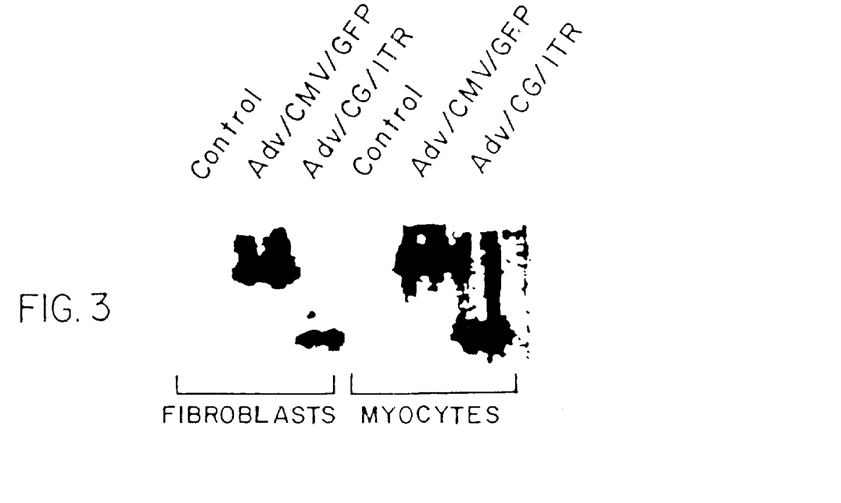
FIG. 3 shows a Southern-blot analysis of the relative cell-type specific transcription of GFP in cultured cells following adenovirus infection. DNA from control or infected cells were digested with NotI and XhoI restriction enzymes and the GFP expression was detected at approximately 3.0 kb size for Adv/CMV/GFP and 760 bases for Adv/CG/ITR.

To ensure that the observed cardiomyocyte restricted expression of Adv/CG/ITR vector was at the transcriptional level rather than secondary to an effect of infectivity, a standard Southern-blot analysis was performed using DNA samples from infected fibroblasts and myocytes. As seen in FIG. 3, viral DNA was present at comparable levels in both cardiomyocytes and fibroblasts infected with either Adv/CMV/GFP or Adv/CG/ITR vectors. These results confirm that the transcriptional activity of the CARP promoter is suppressed in the context of the adenoviral genome and that the inclusion of ITR sequences from AAV allows retention of cardiac restricted cell-type specificity of the CARP promoter in cultured cells.

EXAMPLE 2

In vivo Cardiac Restricted Transgene Expression Mediated by the Adv/CG/ITR Vector in Neonatal Mouse Heart In order for the present invention to be viable as a method of gene therapy for the treatment of inherited and acquired heart disease, it is important to establish that cell type specificity of the Adv/CG/ITR vector, demonstrated in vitro, can also direct tissue targeted transgene expression in vivo. To test this, approximately $2 \times 10^9$ adenovirus particles were injected directly into the heart muscle of day-old mice. Following direct administration of Adv/CMV/ITR vectors into the cardiac cavity, the level of infection was measured to be approximately 10% with a distribution concentrated primarily in the epicardium of the ventricular wall. In addition, a high level of GFP expression was also detected in the liver of the infected animals. This observation agrees with many earlier published studies where it has been established that the delivery of the recombinant adenovirus through the systemic circulation always lead to high levels of infection in the liver and other non-cardiac tissue. Similar to previous observations, direct intracardiac injection of the Adv/CG vector resulted in no detectable GFP in any tissue, including the heart. As predicted, the adenoviral vector of the present invention, Adv/CG/ITR, gave rise to a significant level of GFP expression in heart tissue but a much lower expression in liver and other non-cardiac tissue.

Figure 4:
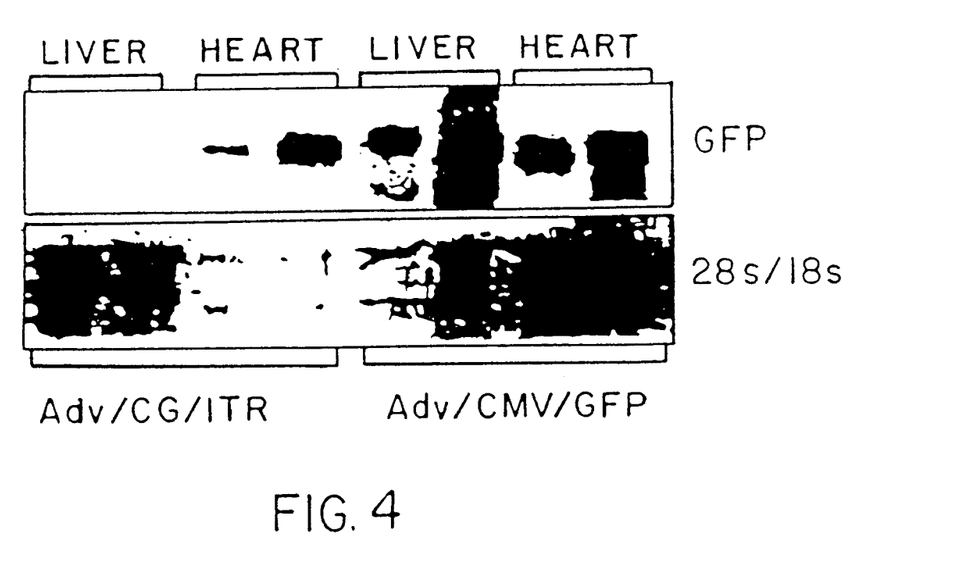
FIG. 4 shows a Northern-blot analysis of the level of GFP transcription in mouse heart and liver following intracardiac injection of adenovirus vectors.

To further evaluate tissue specific expression of the transgene, Northern-blot analyses were performed on RNA samples prepared from the heart and liver of the infected mice. The results of the analysis is shown in FIG. 4. In Adv/CMV/GFP injected animals, GFP mRNA was detected at high levels in both the heart and liver confirming the results generated by the Northern-blot analysis. In the Adv/CG/ITR injected mice, however, GFP mRNA was detected primarily in the heart and at a significantly lower level in the liver. The inclusion of AAV ITR in the adenovirus vector, as prescribed in the present invention, enhances the tissue-specificity of transgene expression in vivo, making the adenovirus vector of this invention suitable for use in the delivery of gene therapeutic agents.

EXAMPLE 3

Cardiac-restricted Transgene Expression Mediated by the Adv/CG/ITR Vector in Cultured Mouse Embryos The tissue-specific gene transfer properties of the present invention can also be applied to study gene function during embryonic cardiac development. To demonstrate the ability of targeted gene expression, in developing heart tissue, using tissue specific adenoviral vectors, approximately 2×10$^8$ particles of each of the recombinant adenovirus vectors, Adv/CMV/GFP, Adv/CG and Adv/CG/ITR were microinjected into the cardiac cavities of developing mouse embryos at 11 days post coitum. Following an additional 25 hours of culturing after initial injection of the adenoviral vectors, GFP expression was evaluated. Injection of the Adv/CMV/GFP vector resulted in high relative levels of GFP expression in in the developing heart as well as in a wide range of other tissues. This wide spread expression pattern confirms earlier evidence indicating that the Adv/CMV/GFP vector is capable of directing transgene expression in a broad range of tissues and that transgene expression is most likely dictated by the distribution of viral particles in the developing embryo. Following injection of the recombinant Adv/CG vector, analysis by fluorescent photomicroscopy revealed no GFP expression in any part of the embryo which correlated with in vitro results derived from cultured cells and in vivo data from neonatal mice studies. Injection of Adv/CG/ITR vector gave rise to the expression of GFP in cardiac tissue with no ectopic expression, detectable by fluorescent photomicroscopy, in other tissues. Specifically, GFP expression was at the highest level in the atrium.

These results demonstrate that inclusion of the ITR sequences from AAV, as in the Adv/CG/ITR vector construct of the present invention, eliminates ectopic expression of the transgene, and allows for cardiac tissue specific expression, following direct ventricular injection of the adenoviral vector into developing embryos. Such tissue specific expression, directed by the Adv/CG/ITR vector of the present invention, can be applied to the development of other recombinant adenoviral vectors that contain ITR sequences from AAV and may confer cardiac specific expression of a therapeutic transgene in the treatment of cardiac damage and dysfunction.

Although the invention has been described with reference to the examples provided above, it should be understood that various modifications can be made without departing from the spirit of the invention. Accordingly, the invention is limited only by the following claims.

What is claimed is:

1. A human type-5 recombinant adenovirus vector, which has tissue specific transcription of a transgene, the adenovirus vector comprising: the transgene; a cardiomyocyte-restricted ankyrin repeat protein (CARP) promoter; and inverted terminal repeat (ITRs) sequences from human adeno-associated virus (AAV); wherein the transgene, promoter, and ITRs are operably linked.

2. The human type-5 recombinant adenovirus vector of claim 1, wherein the inverted terminal repeat sequences from AAV comprise two copies of the inverted terminal repeat sequence.

3. The human type-5 recombinant adenovirus vector of claim 2, wherein the two copies of inverted terminal repeat sequence from AAV comprise the left end and right end inverted terminal repeat sequence.

4. The human type-5 recombinant adenovirus vector of claim 3, wherein the left end and right end inverted terminal repeat sequence from AAV comprise the 5' end and the 3' end inverted terminal repeats respectively.

* * * * *